(12) United States Patent
Hayashizaki et al.

(10) Patent No.: US 6,342,387 B1
(45) Date of Patent: Jan. 29, 2002

(54) METHOD FOR ISOLATING DNA

(75) Inventors: Yoshihide Hayashizaki, c/o The Institute of Physical and Chemical Research, Tsukuba Life Science Center, 1-1, Koyadai 3-chome, Tsukuba-shi, Ibaraki 305-0074; Piero Carninci, Tsukuba, both of (JP)

(73) Assignees: RIKEN, Saitama; Yoshihide Hayashizaki, Ibaraki, both of (JP)

( * ) Notice: Subject to any disclaimer, the term of this patent is extended or adjusted under 35 U.S.C. 154(b) by 0 days.

(21) Appl. No.: 09/508,119

(22) PCT Filed: Sep. 18, 1998

(86) PCT No.: PCT/JP98/04201

§ 371 Date: Jun. 12, 2000

§ 102(e) Date: Jun. 12, 2000

(87) PCT Pub. No.: WO99/15645

PCT Pub. Date: Apr. 1, 1999

(30) Foreign Application Priority Data

Sep. 22, 1997 (JP) ............................. 9-256795

(51) Int. Cl.$^7$ ................................. C07H 1/08
(52) U.S. Cl. ................... 435/270; 536/25.4; 536/25.41; 536/25.42
(58) Field of Search .................. 435/270; 536/25.4, 536/25.41, 25.42

(56) References Cited

U.S. PATENT DOCUMENTS

| | | | | |
|---|---|---|---|---|
| 4,833,239 A | * | 5/1989 | DeBonville et al. | 536/27 |
| 5,010,183 A | | 4/1991 | Macfarlane | 536/25.4 |
| 5,204,382 A | | 4/1993 | Wallace et al. | 523/115 |
| 5,234,809 A | * | 8/1993 | Boom et al. | 435/91.2 |
| 5,342,931 A | | 8/1994 | Woodard et al. | 536/25.4 |
| 5,547,677 A | * | 8/1996 | Wright | 424/401 |
| 5,596,092 A | | 1/1997 | Schneider | 536/25.4 |
| 5,660,984 A | * | 8/1997 | Davis et al. | 435/6 |
| 5,948,826 A | * | 9/1999 | Terada et al. | 521/27 |
| 5,990,301 A | * | 11/1999 | Colpan et al. | 536/25.4 |

OTHER PUBLICATIONS

English Language Abstract of JP 4–360686.
English Language Abstract of JP 8–23976.
English Language Abstract of JP 7–250681.
Schneider , "Simplified Isolation and Quantitation of Cytoplasmic DNA from Rat Liver", *Analytical Biochemistry*, 103, pp. 413–418 (1980).
Tong et al., "Solid–Phase Method for the Purification of DNA Sequencing Reactions", *ANal. Chem.*, 64, pp. 2672–2677 (1992).
Boom et al., "Rapid and Simple Method for Purification of Nucleic Acids" *Journal of Clinical Microbiology*, vol. 28, No. 3, pp. 495–503 (Mar. 1990).
English Translation of Natkinis et al., "Two Simple Methods for Isolation of DNA from Various Sources Using Cetavlon", *Biokhimiya*, 42(10), p. 1783–1790 (1977).
Ellington. 1993. Purification of oligonucleotides using denaturing polyacrylamide gel electrophoresis. pp. 2.12.1–2.12.5. in Ausubel et al., eds. Current Protocols in Molecular Biology. John Wiley & Sons, Inc.*
Reichardt et al. 1994. Preparation of genomic DNA from plant tissue. pp. 2.3.7.–2.3.7. in Ausubel et al., eds. Current Protocols in Molecular Biology, John Wiley & Sons, Inc.*
Budelier. 1993. Purification of DNA by anion–exchange chromatography. pp. 2.14.1–2.14.8. in Ausubel et al., eds. Current Protocols in Molecular Biology. John Wiley & Sons, inc.*
Richards. 1993. Separation of double– and single–stranded nucleic acids using hydroxylapatite chromatography. pp. 2.13.1–213.3 in Ausubel et al., eds. Current Protocols in Molecular Biology. John Wiley & Sons, Inc.*
Hjelmeland. 1990. Solubilization of native membrane proteins. pp. 253 and 257. in Deutscher, et. Guide to protein purification. Academic Press, Inc.*
Eisenberg et al. 1990. Purification of DNA–binding proteins by site–specific DNA affinity chromatography. pp. 521,524, 525. in Deutscher, et. Guide to protein purification. Academic Press, Inc.*

* cited by examiner

*Primary Examiner*—Robert A. Schwartzman
*Assistant Examiner*—Bronwen M. Loeb
(74) *Attorney, Agent, or Firm*—Greenblum & Bernstein, P.L.C.

(57) ABSTRACT

A method for isolating DNA contained in a biological sample, including: lysing a DNA-containing biological sample and forming a DNA-bound carrier by placing a lysing solution, including the DNA-containing biological sample, a salt, and a cationic surfactant, and having a salt concentration higher than the DNA precipitation inhibition-initiating concentration, into contact with a DNA-binding carrier to bind DNA to the DNA-binding carrier to form the DNA-bound carrier; separating the DNA-bound carrier from other components; dissociating the bound DNA from the DNA-binding carrier; and recovering dissociated DNA. By the method, DNA purified with no preliminary treatment of a biological sample can be recovered at a high yield.

40 Claims, 2 Drawing Sheets

METHOD FOR ISOLATING DNA

TECHNICAL FIELD

The present invention relates to a method for isolating DNA from biological samples such as blood, cells and biological tissues.

BACKGROUND OF THE INVENTION

Transformation of microorganisms such as *Escherichia coli* and the like, the culturing of the resulting transformant, and the recovery of a desired plasmid DNA from the proliferating transformant have been carried out routinely in the field of genetic engineering. For the purpose of collecting DNA information concerning cancer and genetic diseases and using the DNA information for diagnosis, additionally, DNAs from biological samples such as blood, cells and biological tissues are recovered.

The method for more simply recovering and purifying plasmid DNAs from transformants includes, for example, methods described in Japanese Patent Laid-open No. 360686/1992, Japanese Patent Laid-open No. 23976/1996, R. Boom et al., J. Clin. MicroBiol. Vol. 28, No. 3, p. 495–503, and Japanese Patent Laid-open No. 250681/1995.

Among them, the chaotropic ion method described in R. Boom et al., J. Clin. MicroBiol. Vol. 28, No. 3, p. 495–503 is an excellent method for isolating DNA alone, comprising separating RNA and DNA comprised in microorganisms from each other by using DNA-absorbing carrier and chaotropic solution in combination. This method is also described by the Japanese Patent Laid-open No. 250681/1995 wherein the purification of only DNA from a microbial organism is carried out using two kinds of cartridges.

When the chaotropic ion method was used for biological samples such as blood, cells and biological tissues as subjects, DNAs from these biological samples could never be isolated without preliminary treatment of the biological samples, differing from the case of microorganisms. When carrying out the isolation of DNA from blood, proteins are also captured on the carrier by the chaotropic ion method, so that the DNA cannot be efficiently isolated or recovered.

A method for precipitating DNA comprised in blood in the presence of 0.5 to 0.6 M sodium chloride and a cationic surfactant alkylbenzyldimethylammonium salt is disclosed in U.S. Pat. No. 5,010,183.

Using this method, however, DNA cannot be recovered, when blood is used as the biological sample without any preliminary treatment (separation) or the like. The method requires preliminary treatment, for example leukocyte separation from blood. Furthermore, DNA yield or purity is not high.

It is an object of the present invention to provide a method for recovering purified DNA at a high DNA yield, using a biological sample without preliminary treatment.

It is an additional object of the invention to provide a method for recovering purified DNA at a high DNA yield, using a biological sample without preliminary treatment, wherein the method does not require complicated procedures such as centrifugation or extraction but requires the use of apparatuses of simpler structures and less procedures, so that the method can be automated. In view of the above, the method of the present invention does not require centrifugation between steps. For instance, the present invention does not require centrifugation between lysing a DNA-containing biological sample and forming a DNA bound carrier, which lysing and forming are discussed in more detail below. Similarly, the present invention does not require centrifugation between combining in a lysing solution a DNA-containing biological sample, a salt and a cationic surfactant, and supplying the lysing solution to a column with a DNA-binding carrier, which combining and supplying are discussed in more detail below. In view of this and other disclosure, the method of the present invention may be conducted without phosphate.

SUMMARY OF THE INVENTION

The invention relates to a method (first method) for isolating DNA from a biological sample, comprising
  (a) putting a lysing solution, comprising a DNA-containing biological sample, a salt, and a cationic surfactant, and having a salt concentration the same or higher than the concentration initiating the inhibition of DNA precipitation (hereinafter referred to as precipitation inhibition-initiating concentration) into contact with a DNA-binding carrier to allow the DNA comprised in the biological sample to bind to the DNA-binding carrier;
  (b) separating the DNA-bound carrier from other components;
  (c) dissociating the bound DNA from the separated carrier; and
  (d) recovering the dissociated DNA.

Furthermore, the invention relates to a method (second method) for isolating DNA from a biological sample, comprising
  (A) supplying a solution, comprising a DNA-containing biological sample, a salt, and a cationic surfactant, and having a salt concentration the same or higher than the precipitation inhibition-initiating concentration, into a column with a DNA-binding carrier arranged on a membrane filter, said membrane having a solution retention potency and a solution permeation potency under aspiration, to allow the DNA in the biological sample to bind to the DNA-binding carrier;
  (B) separating the DNA-bound carrier from other components, by removing the lysing solution under aspiration from the column;
  (C) supplying a DNA-dissociating solution into the column, to dissociate DNA from the carrier; and
  (D) recovering a solution comprising the dissociated DNA, by separating the dissociating solution under aspiration from the column.

PREFERABLE EMBODIMENTS FOR CARRYING OUT THE INVENTION

DNA Isolation Method (First Method)

Figure 1:
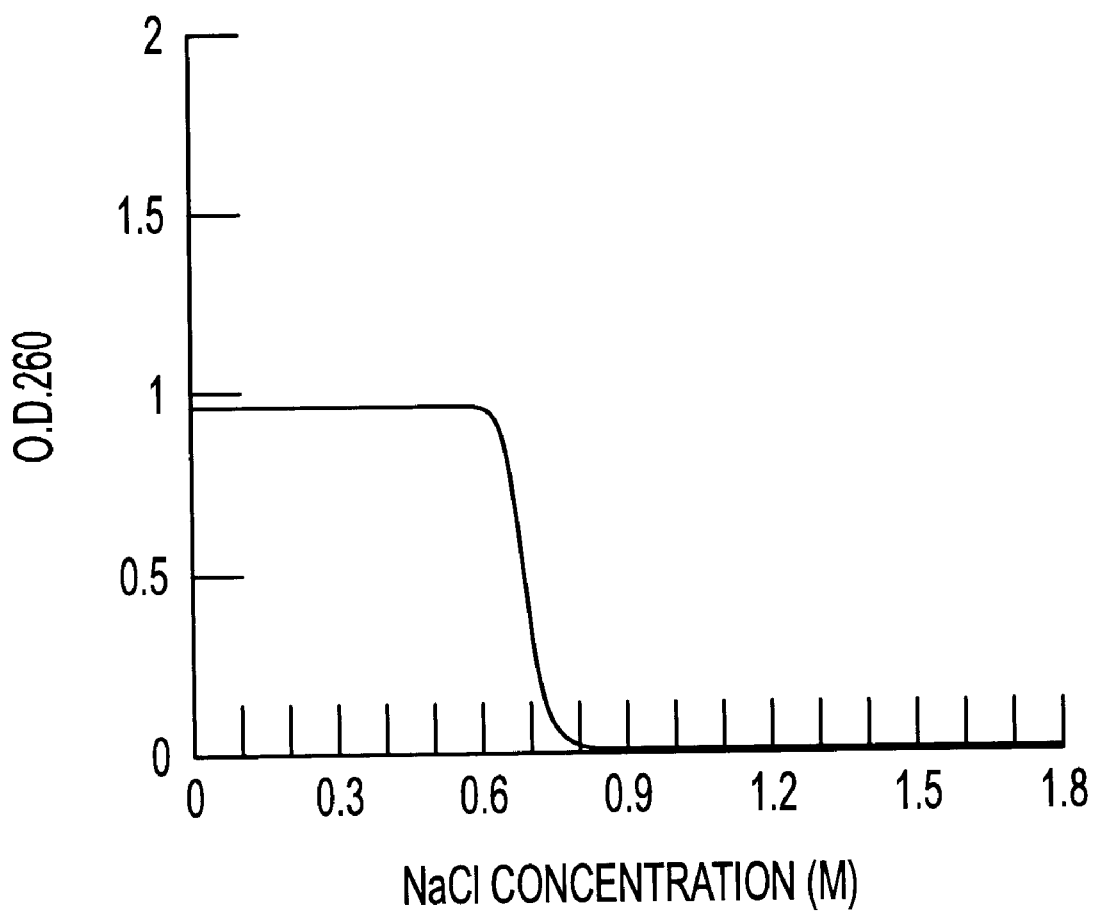
FIG. 1 is a graph depicting the relation between the salt concentration and absorbance at 260 nm, as observed in a reference example.

At the step (a), a lysing solution, comprising a DNA-containing biological sample, a salt and a cationic surfactant, and having a salt concentration the same or higher than the precipitation inhibition-initiating concentration is put into contact with a DNA-binding carrier to allow the DNA comprised in the biological sample to bind to the DNA-binding carrier. The incubation time of contact with the DNA-binding carrier is determined appropriately, depending on the composition and amount of the lysing solution and the kind and amount of the DNA-binding carrier, but generally, about 3 to 5 minutes are sufficient for the incubation time. Additionally, the incubation can be carried out without heating, but if necessary under appropriate heating, preferably, under condition such that the denaturation of DNA can be avoided.

The DNA-containing biological sample may be, for example, blood, a cell or a biological tissue. The cell may be a eukaryotic cell or a bacterial cell. Blood is a biological sample with laborious handleability, so that the isolation of DNA from blood is difficult by conventional methods. According to the method of the invention, DNA can be isolated therefrom. The concentration of a DNA-containing biological sample in the lysing solution can appropriately be determined, depending on the kind of the biological sample, the composition of lysing solution and the kind of the DNA-binding carrier used.

The cationic surfactant includes, for example, at least one surfactant selected from the group consisting of cetyltrimethylammonium bromide, tetradecyltrimethylammonium bromide, dodecyltrimethylammonium bromide, and cetylpyridiniumbromide. However, the cationic surfactant is not limited to these surfactants. Additionally, the concentration of the cationic surfactant is determined, taking into account the critical micelle concentration, which is generally within a range of 0.01 to 10%.

The salt may be an inorganic acid salt (for example, chloride, nitrate, sulfate, phosphate, and the like) and an organic acid salt (for example, acetate, citrate and the like). More specifically, the salt includes NaCl and other salts (for example, all salts of Na, K, and Li, in combination with Cl, Br, acetic acid, and formic acid).

At the step (a), the salt concentration of the solution comprising a DNA-containing biological sample, a salt, and a cationic surfactant is set up above the DNA precipitation inhibition-initiating concentration. The DNA comprised in the solution can thereby be selectively bound to the DNA-binding carrier. The precipitation inhibition-initiating concentration varies, depending on the kind of salt comprised in the solution; and also depending on the kinds and concentrations of other components, even in case that the same salt is comprised. Therefore, the precipitation inhibition-initiating concentration can appropriately be determined for each salt. In case of sodium chloride, for example, the precipitation inhibition-initiating concentration is about 0.6 M, as described below.

Taking into account the binding efficiency of DNA in the solution to the DNA-binding carrier, the salt concentration of the solution is preferably between the same and 2-fold concentration of the precipitation inhibition-initiating concentration or the salt concentration for solubilizing the total DNA, whichever is higher. Like the precipitation inhibition-initiating concentration, the salt concentration for solubilizing the total DNA varies, depending on the kind of the salt comprised in the solution; and also varies depending on the kinds and concentrations of other components, even in the case that the same salt is used. Therefore, the salt concentration can appropriately be determined for each salt. In the case of sodium chloride, for example, the salt concentration for solubilizing the total DNA is about 0.8 M, as described below.

In the case that the biological sample comprises at least linear double-stranded DNA and linear single-stranded DNA, the linear double-stranded DNA selectively binds the DNA-binding carrier at the step (a), and is selectively isolated from the biological sample. In this case, the lysing solution preferably additionally comprises a hydrogen bond-cleaving agent. The hydrogen bond-cleaving agent includes for example urea and formaldehyde. The concentration of urea may be for example 10% (w/v) or more.

The DNA-binding carrier includes a mesh filter, beads or a powder, comprising a material selected from the group consisting of glass, silica gel, anion exchange resin, hydroxyapatite and celite. In view of the above, in some cases, the DNA-binding carrier is not hydroxyapatite.

At the step (b), the DNA-bound carrier is filtered or centrifuged, and subsequently, the resulting carrier is washed with a rinse solution having a salt concentration higher than the precipitation inhibition-initiating concentration, to separate the DNA-bound carrier from other components. The rinse solution preferably has a salt concentration between the same and 2-fold concentration of the precipitation inhibition-initiating concentration or the salt concentration for solubilizing the total DNA, whichever is higher. Furthermore, the carrier is preferably washed sequentially in a rinse solution comprising an aqueous solution comprising a cationic surfactant and in a rinse solution comprising an aqueous solution comprising a volatile organic solvent. The use of the rinse solution comprising an aqueous solution comprising a cationic surfactant enables the removal of impurities from the carrier, and then the use of a rinse solution comprising an aqueous solution comprising a volatile organic solvent enables the removal of the cationic surfactant from the carrier. Herein, the volatile solvent is preferably ethanol because denaturation of the DNA bound to the carrier is avoidable and rapid evaporation after washing can be carried out.

After washing, the carrier can be dried, if necessary, but excess drying occasionally prevents the dissociation of the DNA bound to the carrier.

The rinse solution and/or the lysing solution is preferably a solution comprising glycerol, in order to avoid the adsorption of the DNA-binding carrier to each other, which causes difficulty in handling. The amount of glycerol to be added is for example within a range of 1 to 50%.

At the step (c), the separated carrier is mixed with a lysing solution with the conditional composition for solubilizing DNA, to dissociate the bound DNA from the carrier. The lysing solution with the conditional composition for solubilizing DNA may be, for example, water or heated water, while the temperature of the heated water is a temperature appropriately selected for prompt solubilization of DNA.

At the step (d), a mixture of the solution comprising the dissociated DNA and the carrier is subjected to solid-liquid separation, to recover the dissociated DNA in the form of a solution. The solid-liquid separation may be, for example, centrifugation or filtration.

DNA Isolation Method (Second Method)

At step (A), a solution comprising a DNA-containing biological sample, a salt, and a cationic surfactant having a concentration of the salt higher than the precipitation inhibition-initiating concentration, is supplied to a column with a DNA-binding carrier arranged on a membrane filter, the filter having a solution retention potency and a solution permeation potency under aspiration, to allow the DNA in the biological sample to bind to the DNA-binding carrier.

The second method of the invention has many steps substantially in common to the first method, except for the use of a column in which the DNA-binding carrier is arranged on the membrane filter, the filter having a solution retention potency and a solution permeation potency under aspiration.

The above column is satisfactorily a single pipe (tube) with one opening arranged with the membrane filter or a plate of a constant thickness with multiple through-holes arranged therein and with a membrane filter arranged over one opening of each such through-hole. In the latter case, DNA isolation from multiple samples comprising DNA can be carried out concurrently in multiple columns arranged through a plate, so that various samples can advantageously be treated rapidly.

The DNA-binding carrier includes a mesh filter, beads or a powder, comprising a material selected from the group consisting of glass, silica gel, anion exchange resin, hydroxyapatite and celite.

Additionally, the membrane filter has a solution retention potency and a solution permeation potency under aspiration. In other words, the membrane filter has a performance such that the solution can be retained on the membrane filter under no aspiration, while the retained solution is discharged through the membrane filter by aspiration from the side opposite to the side for the retention of the solution. By using such membrane filter, advantageously, the incubation time of the DNA-binding carrier with the DNA-containing solution, the discharge of the solution, the washing and the like can be carried out under control. Particularly because no centrifugation is required for solid-liquid separation, advantageously, the method can readily be automated.

The incubation time in contact with the DNA-binding carrier can appropriately be determined, depending on the composition and amount of the lysing solution, and the kind and amount of the DNA-binding carrier, but generally, about 3 to 5 minutes are sufficient for the incubation time. Additionally, the incubation can be carried out with no heating, but if necessary can be carried out under appropriate heating, preferably, under condition such that the denaturation of DNA can be avoided.

The DNA-containing biological sample may be, for example, blood, a cell or a biological tissue. The cell may be a eukaryotic cell or a bacterial cell. Blood is a biological sample with laborious handleability, so that DNA isolation from blood is difficult by conventional methods. According to the method of the invention, DNA can be isolated therefrom. The concentration of a DNA-containing biological sample in the lysing solution can appropriately be determined, depending on the kind of the biological sample, the composition of the lysing solution and the kind of the DNA-binding carrier.

At the step (A), the salt concentration of the solution comprising a DNA-containing biological sample, a salt, and a cationic surfactant is set up above the DNA precipitation inhibition-initiating concentration. The DNA comprised in the solution can thereby be bound to the DNA-binding carrier selectively. The precipitation inhibition-initiating concentration varies, depending on the kind of the salt comprised in the solution, and also varies depending on the kinds and concentrations of other components, even in the case that the same salt is used. Therefore, the precipitation inhibition-initiating concentration can appropriately be determined for each salt. In the case of sodium chloride, for example, the precipitation inhibition-initiating concentration is about 0.6 M, as described below.

Taking into account the binding efficiency of DNA in the solution to the DNA-binding carrier, the salt concentration is preferably between the same and 2-fold concentration of the precipitation inhibition-initiating concentration or the salt concentration for solubilizing the total DNA, whichever is higher. Like the precipitation inhibition-initiating concentration, the salt concentration for solubilizing the total DNA varies, depending on the kind of salt in the solution; and also varies depending on the kinds and concentrations of other components even in the case that the same salt is used. Therefore, the salt concentration can appropriately be determined for each salt. In the case of sodium chloride, for example, the salt concentration for solubilizing the total DNA is about 0.8 M, as described below.

In the case that the biological sample comprises at least linear double-stranded DNAs and linear single-stranded DNAs, the linear double-stranded DNA selectively binds the DNA-binding carrier at the step (A), and is selectively isolated from the biological sample. In this case, the lysing solution preferably additionally comprises a hydrogen bond-cleaving agent. The hydrogen bond-cleaving agent includes for example urea and formaldehyde. The concentration of urea may be for example 10% (w/v) or more.

At the step (B), the DNA-bound carrier is separated from other components, by removing the lysing solution. The DNA-bound carrier is separated by filtration through the membrane filter under aspiration from the column, and the resulting carrier is washed with a rinse solution having a salt concentration higher than the precipitation inhibition-initiating concentration. The rinse solution preferably has a salt concentration between the same and 2-fold concentration of the precipitation inhibition-initiating concentration or the salt concentration for solubilizing the total DNA, whichever is higher. Furthermore, the carrier is preferably washed sequentially in a rinse solution comprising an aqueous solution comprising a cationic surfactant and in a rinse solution comprising an aqueous solution comprising a volatile organic solvent. The use of the rinse solution comprising an aqueous solution comprising a cationic surfactant enables the removal of impurities from the carrier, and then the subsequent use of the rinse solution comprising an aqueous solution comprising a volatile organic solvent enables the removal of the cationic surfactant from the carrier. Herein, the volatile organic solvent is preferably ethanol because denaturation of the DNA bound to the carrier is avoidable and rapid evaporation after washing can be carried out.

After washing, the carrier can be dried, if necessary, but excess drying occasionally prevents the dissociation of DNA bound to the carrier.

The rinse solution and/or the lysing solution is preferably a solution comprising glycerol, in order to avoid the adsorption of the DNA-binding carrier to each other, which causes difficulty in handling. The amount of glycerol to be added is for example within a range of 1 to 50%.

At the step (C), DNA is dissociated from the carrier, by supplying a DNA-dissociating solution to the column. The separated carrier is mixed with a lysing solution with the conditional composition for solubilizing DNA, to dissociate the bound DNA from the carrier. The lysing solution with the conditional composition for solubilizing DNA maybe for example water or heated water, while the temperature of the heated water is a temperature appropriately selected for prompt solubilization of DNA.

At the step (D), a solution comprising the dissociated DNA is recovered, by separating the dissociating solution from the column under aspiration.

The second method of the invention is advantageous in that the method can be promptly automated, because the separation of the solution from the carrier can be done by filtration under aspiration.

EXAMPLES

The invention is further described in the following examples.

Reference Example (Measurement of precipitation inhibition-initiating concentration)
Solution Composition
  0 to 1.5 M NaCl
  30 mM Tris (pH 8.5)
  15 mM EDTA
  0.5% CTAB (cetyltrimethylammonium bromide)
  Genomic DNA 50 μg/ml Individual solutions with the aforementioned composition at NaCl concentrations increasing in 0.05 M increments from 0 to 1.5 M were prepared; and starting of precipitation was observed. After subsequent centrifugation and supernatant discarding, the resulting precipitate was again dissolved in water; so as to assay the quantity of DNA, the absorbance at 260 nm was measured. The results are shown in FIG. 1. The concentration at which the precipitation started was defined as precipitation start concentration; and the concentration at which the amount of precipitate was retained constant was defined as the precipitation inhibition-initiating concentration of the solution. The precipitation start concentration of the solution was 0.7 M and the precipitation inhibition-initiating concentration was 0.6 M.

Example 1

1) 750 μl of lysing solution A with the following composition were added to whole blood of 300 μl (for a microfilter of Eppendorf tube size)
Lysing solution A:
  Urea 25% (w/v)
  CTAB (cetyltrimethylammonium bromide) 0.45%
  NaCl 0.8 M
  EDTA 15 mM
  Tris pH 7.1, 80 mM
  Glycerol 10% (v/v)
  Diatomaceous earth (manufactured by Sigma, Co; acid rinsed and calcined) 1% (w/v)
  Cellulose (manufactured by Sigma, Co,; alpha-cellulose) 0.3%

Glycerol advantageously allows the easy manipulation of silica matrix and avoids the packing thereof.

The solution comprises a DNA-binding matrix and was agitated with a magnetic stirrer prior to use. The DNA-binding matrix was dissolved together with inert matrices, so as to allow the prompt resuspension of the DNA-binding matrix per se and thereby enhance the reproducibility of the extraction.

After addition of the lysing solution, the mixture was completely mixed together by inversion or weak agitation. The solubilization reaction can be carried out at room temperature or under mild heating, namely at 37° C. The length of the incubation was 5 minutes.

2) The mixture solution was transferred on an appropriate filter, which was then subjected to reduced pressure. The transfer of the whole lysing reaction solution on the filter enables the simplification of the manipulation. Finally, the a contaminating substances were washed off, so that DNA was retained on the DNA-binding matrix.

3) Rinse solution A of 900 μl having the following composition was added to the filter. The volume 900 μl of the rinse solution A to fill the filter funnel was a sufficient volume to completely wash the whole filter. Under reduced pressure, the rinse solution was removed. Through this step, the residual contaminants present in the filter were removed. This step can optionally be repeated. The reproducibility of the manipulation can thereby be enhanced.

Rinse solution A:
  Urea 25%
  CTAB 0.45%
  NaCl 0.55 M
  EDTA 15 mM
  Tris pH 7.1, 80 mM
  Glycerol 10% (v/v)

4) After the removal of the liquid phase, 900 μl of rinse solution B were added to the filter. The cationic detergent can be removed from the filter and from the DNA-binding resin, by using the rinse solution B (alcoholic saline). After the addition of the solution the incubation for several minutes (2 to 4 minutes) was carried out, so as to promote complete ion exchange prior to application of reduced pressure. This step can be repeated, optionally, so as to raise the reproducibility of the manipulation. A reduced pressure was applied until the rinse solution was removed. Optionally, the filter was further washed with 70% ethanol, satisfactorily, so as to totally remove the trace amount of the salts contaminating in the rinse solution B.

Additionally 900 μl of the rinse solution B were added, followed by incubation at room temperature for 4 minutes. The rinse solution was removed by re-application of reduced pressure.

Rinse solution B:
  Triton X100, 0.069%
  Tris, pH 8.5, 300 mM
  EDTA 7.5 mM
  NaCl 600 mM
  Sodium acetate 600 mM
  Glycerol 30% (v/v)

(A 2-fold volume of ethanol was added to the resulting solution prior to use, to adjust the solution to a final ethanol concentration of 66%.)

5) The filter comprising the biological sample was dried under reduced pressure and in aeration for 3 to 5 minutes, until ethanol was removed (optionally, instead of this step, centrifugation process was satisfactorily carried out).

6) 50 to 100 μl of water (preliminary heated to 60 or 70° C.) were added to the filter. The filter was transferred in a centrifuge tube. The contents were mixed until the DNA-binding matrix turned into fine particles by agitation (this procedure is sometimes an important step); incubated at room temperature for 2 minutes and centrifuged in a micro-centrifugal machine for 30 seconds. The isolated and resuspended DNA can be used as it is.

Total time: 10 to 25 minutes, depending on the application of such optional steps.

Example 2

Figure 2:
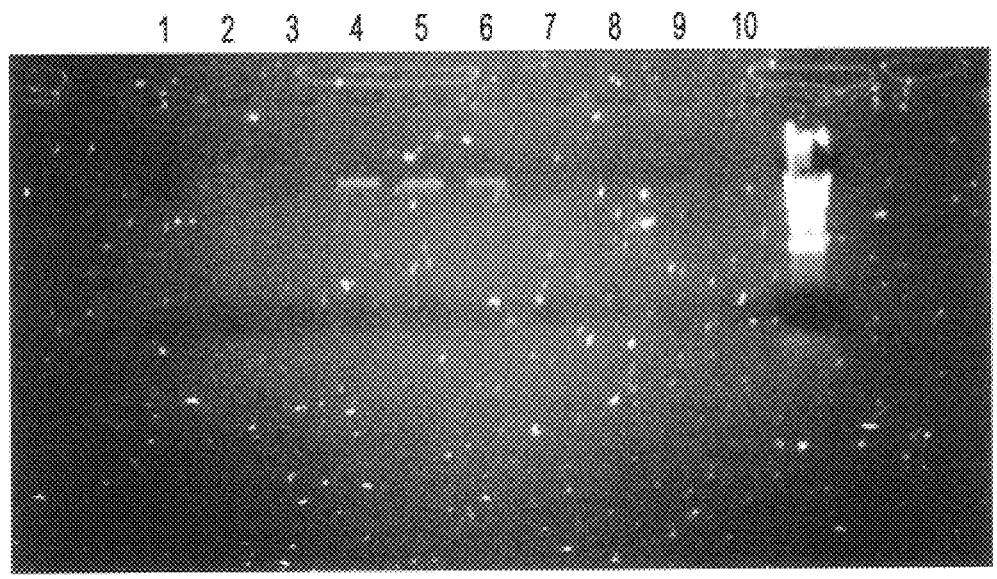
FIG. 2 shows the electrophoresis results observed in Example 2.

DNA was isolated in the same manner as in Example 1, except for the modification of the NaCl concentration in the lysing solution between 0 and 1.8 M. The aqueous resuspended DNA solution was electrophoresed. The results are shown in FIG. 2. Consequently, it is indicated that DNA was isolated well at the NaCl concentration within a range of 0.6 to 1.0 M. Within a range of 0 to 0.4 M, the resulting DNA was contaminated with the protein in the biological sample, indicating that the purification was insufficient. In the case that the NaCl concentration was 1.2 M or more, no DNA could be recovered. This was possibly ascribed to no adsorption of DNA on the carrier.

In accordance with the invention, a method for recovering purified DNA at a high DNA yield using biological samples without preliminary treatment can be provided.

The inventive method does not require complicated procedures such as centrifugation or extraction but requires the use of apparatuses of simpler structures and less procedures so that the method can be automated, if necessary.

What is claimed is:

1. A method for isolating DNA contained in a biological sample, comprising:

lysing a DNA-containing biological sample and forming a DNA-bound carrier by placing a lysing solution, comprising the DNA-containing biological sample, a salt, and a cationic surfactant, and having a salt concentration higher than the DNA precipitation inhibition-initiating concentration, into contact with a DNA-binding carrier to bind DNA to the DNA-binding carrier to form the DNA-bound carrier, without centrifugation between the lysing and the forming;

separating the DNA-bound carrier from other components;

dissociating the bound DNA from the DNA-binding carrier; and recovering dissociated DNA.

2. The method of claim 1, wherein the salt concentration of the lysing solution has a lower limit of the concentration of the DNA precipitation inhibition-initiating concentration, and wherein the salt concentration of the lysing solution has an upper limit of the higher of the salt concentration for solubilizing the total DNA and 2-fold the concentration of the DNA precipitation inhibition-initiating concentration.

3. The method of claim 1, wherein the DNA-containing biological sample comprises blood, a cell, or a biological tissue.

4. The method of claim 1, wherein the cationic surfactant comprises at least one of cetyltrimethylammonium bromide, tetradecyltrimethylammonium bromide, dodecyltrimethylammonium bromide, and cetylpyridinium bromide.

5. The method of claim 1, wherein the DNA-containing biological sample comprises at least linear double-stranded DNA and linear single-stranded DNA, and wherein placing the lysing solution into contact with the DNA-binding carrier comprises selectively binding the linear double stranded DNA to the DNA-binding carrier, to selectively isolate linear double-stranded DNA from the DNA-containing biological sample.

6. The method of claim 1, wherein the DNA-binding carrier comprises mesh filter, beads, a fiber, or a powder, the DNA-binding carrier further comprising a material comprising one of glass, silica gel, anion exchange resin, hydroxyapatite, celite, cellulose, and diatomaceous earth.

7. The method of claim 1, wherein placing the lysing solution into contact with the DNA-binding carrier is performed without heating.

8. The method of claim 1, wherein separating the DNA-bound carrier from other components comprises filtration or centrifugation, and subsequently washing the DNA-bound carrier with a rinse solution having a salt concentration higher than the precipitation inhibition-initiating concentration, to separate the DNA-bound carrier from other components.

9. The method of claim 1, wherein after separating the DNA-bound carrier from other components, dissociating the bound DNA from the DNA-binding carrier comprises mixing the DNA-bound carrier with a solution comprising a composition that solubilizes DNA to dissociate the bound DNA from the DNA-binding carrier.

10. The method of claim 1, wherein dissociating the bound DNA from the DNA-binding carrier results in a solution comprising dissociated DNA, and wherein recovering dissociated DNA comprises subjecting the solution comprising dissociated DNA to solid-liquid separation to recover dissociated DNA in the form of a solution.

11. The method of claim 1, wherein the DNA-containing biological sample is not pretreated by centrifugation.

12. The method of claim 1, wherein the DNA-binding carrier is not hydroxyapatite.

13. The method of claim 1, wherein the method is conducted without phosphate.

14. The method of claim 5, wherein the lysing solution further comprises hydrogen bond-cleaving agent.

15. The method of claim 8, wherein the rinse solution has a salt concentration having a lower limit of the DNA precipitation inhibition-initiating concentration, and wherein the salt concentration of the rinse solution has an upper limit of the higher of the salt concentration for solubilizing the total DNA and 2-fold the concentration of the DNA precipitation inhibition-initiating concentration.

16. The method of claim 8, wherein the rinse solution further comprises glycerol.

17. The method of claim 8, further comprising washing the DNA-bound carrier in a rinse solution comprising cationic surfactant, and subsequently washing the DNA-bound carrier in a rinse solution comprising an aqueous solution comprising a volatile organic solvent.

18. The method of claim 14, wherein the hydrogen bond-cleaving agent comprises urea or formaldehyde.

19. The method of claim 17, wherein the lysing solution further comprises glycerol.

20. A method for isolating DNA contained in a biological sample, comprising:

combining in a lysing solution a DNA-containing biological sample, a salt and a cationic surfactant, the lysing solution having a salt concentration higher than the DNA precipitation inhibition-initiating concentration, and supplying the lysing solution to a column with a DNA-binding carrier on a membrane filter, the membrane filter having a solution retention potency and a solution permeation potency under aspiration, to allow DNA in the DNA-containing biological sample to bind to the DNA-binding carrier to form a DNA-bound carrier, without centrifugation between the combining and the supplying;

separating the DNA-bound carrier from other components, by removing the lysing solution from the column;

supplying a DNA-dissociating solution to the column, to dissociate DNA from the DNA binding carrier; and recovering a solution comprising dissociated DNA, by separating the DNA-dissociating solution from the column.

21. The method of claim 20, wherein the salt concentration of the lysing solution has a lower limit of the concentration of the DNA precipitation inhibition-initiating concentration, and wherein the salt concentration of the lysing solution has an upper limit of the higher of the salt concentration for solubilizing the total DNA and 2-fold the concentration of the DNA precipitation inhibition-initiating concentration.

22. The method of claim 20, wherein the DNA-containing biological sample comprises blood, a cell, or a biological tissue.

23. The method of claim 20, wherein the cationic surfactant comprises at least one of cetyltrimethylammonium bromide, tetradecyltrimethylammonium bromide, dodecyltrimethylammonium bromide, and cetylpyridinium bromide.

24. The method of claim 20, wherein the DNA-containing biological sample comprises at least linear double-stranded DNA and linear single-stranded DNA, and wherein supplying a lysing solution to a column with a DNA-binding carrier on a membrane filter to allow DNA in the DNA-containing biological sample to bind to the DNA-binding carrier comprises selectively binding the linear double stranded DNA to the DNA-binding carrier, to selectively isolate linear double-stranded DNA from the DNA-containing biological sample.

25. The method of claim 20, wherein the DNA-binding carrier comprises mesh filter, beads, a fiber, or a powder, the DNA-binding carrier further comprising a material comprising one of glass, silica gel, anion exchange resin, hydroxyapatite, celite, cellulose, and diatomaceous earth.

26. The method of claim 20, wherein supplying a lysing solution to a column with a DNA-binding carrier on a membrane filter to allow DNA in the DNA-containing biological sample to bind to the DNA-binding carrier, is performed without heating.

27. The method of claim 20, wherein separating the DNA-bound carrier from other components comprises filtering and subsequently washing the DNA-bound carrier with a rinse solution having a salt concentration higher than the precipitation inhibition-initiating concentration, to separate the DNA-bound carrier from other components.

28. The method of claim 20, wherein the DNA-dissociating solution comprises water.

29. The method of claim 20, wherein the method comprises concurrent isolation of DNA from multiple DNA-containing biological samples through multiple columns arranged on a plate.

30. The method of claim 20, wherein the lysing solution is removed from the column by aspiration.

31. The method of claim 20, wherein the DNA-dissociating solution is separated from the column by aspiration.

32. The method of claim 20, wherein the DNA-containing biological sample is not pretreated by centrifugation.

33. The method of claim 20, wherein the DNA-binding carrier is not hydroxyapatite.

34. The method of claim 20, wherein the method is conducted without phosphate.

35. The method of claim 24, wherein the lysing solution further comprises hydrogen bond-cleaving agent.

36. The method of claim 27, wherein the rinse solution has a salt concentration having a lower limit of the DNA precipitation inhibition-initiating concentration, and wherein the salt concentration of the rinse solution has an upper limit of the higher of the salt concentration for solubilizing the total DNA and 2-fold the concentration of the DNA precipitation inhibition-initiating concentration.

37. The method of claim 27, wherein the rinse solution further comprises glycerol.

38. The method of claim 27, further comprising washing the DNA-bound carrier in a rinse solution comprising cationic surfactant, and subsequently washing the DNA-bound carrier in a rinse solution comprising an aqueous solution comprising a volatile organic solvent.

39. The method of claim 28, wherein the lysing solution further comprises glycerol.

40. The method of claim 35, wherein the hydrogen bond-cleaving agent comprises urea or formaldehyde.

* * * * *

UNITED STATES PATENT AND TRADEMARK OFFICE
CERTIFICATE OF CORRECTION

PATENT NO. : 6,342,387 B1
DATED : January 29, 2002
INVENTOR(S) : Y. Hayashizaki et al.

It is certified that error appears in the above-identified patent and that said Letters Patent is hereby corrected as shown below:

Title Page,
Item [56], References Cited, FOREIGN PATENT DOCUMENTS, the following was omitted and should be included:
-- Japan       4-360686      12/1992
Japan        8-23976       1/1996
Japan        7-250681      10/1995 --

Signed and Sealed this

Twenty-second Day of June, 2004

JON W. DUDAS
*Acting Director of the United States Patent and Trademark Office*